(12) United States Patent
Sugimoto et al.

(10) Patent No.: US 9,149,582 B2
(45) Date of Patent: Oct. 6, 2015

(54) ADMINISTRATION APPARATUS FOR MEDICAL USE

(75) Inventors: Hirofumi Sugimoto, Saijo (JP); Kouichi Matsuda, Niihama (JP); Toshiaki Iio, Saijo (JP); Seiji Kikuchi, Matsuyama (JP); Yoshiki Takeuchi, Touon (JP)

(73) Assignee: Panasonic Healthcare Holdings Co., Ltd., Tokyo (JP)

( * ) Notice: Subject to any disclaimer, the term of this patent is extended or adjusted under 35 U.S.C. 154(b) by 1580 days.

(21) Appl. No.: 12/249,282

(22) Filed: Oct. 10, 2008

(65) Prior Publication Data

US 2009/0062777 A1 Mar. 5, 2009

Related U.S. Application Data

(62) Division of application No. 11/071,466, filed on Mar. 4, 2005, now abandoned.

(30) Foreign Application Priority Data

Mar. 5, 2004 (JP) ................................. 2004-062740

(51) Int. Cl.
*A61M 5/315* (2006.01)
*A61M 5/20* (2006.01)
(Continued)

(52) U.S. Cl.
CPC ............. *A61M 5/31535* (2013.01); *A61M 5/20* (2013.01); *A61M 5/3146* (2013.01); *A61M 5/31541* (2013.01); *A61M 5/31546* (2013.01); *A61M 2005/206* (2013.01); *A61M 2005/208* (2013.01); *A61M 2005/2073* (2013.01); *A61M 2005/2411* (2013.01); *A61M 2005/2496* (2013.01); *A61M 2005/3126* (2013.01); *A61M 2005/31518* (2013.01); *A61M 2005/31588* (2013.01); *A61M 2205/50* (2013.01); *A61M 2205/52* (2013.01);
(Continued)

(58) Field of Classification Search
CPC ..................... A61M 5/31535; A61M 5/31541; A61M 5/31546; A61M 5/31565; A61M 5/31566; A61M 5/31568; A61M 5/3157; A61M 2005/3154; A61M 2005/31588
USPC ........................................ 604/151–155, 890.1
See application file for complete search history.

(56) References Cited

U.S. PATENT DOCUMENTS 1,157,552 A 10/1915 Kispert
1,512,294 A 10/1924 Marcy
4,529,401 A * 7/1985 Leslie et al. ................... 604/131

(Continued)

FOREIGN PATENT DOCUMENTS

CN 2396824 Y 9/2000
EP 0 829 268 3/1998

(Continued)

OTHER PUBLICATIONS

English translation of Chinese Application No. 2396824.

*Primary Examiner* — Andrew Gilbert
(74) *Attorney, Agent, or Firm* — Wenderoth, Lind & Ponack, L.L.P.

(57) ABSTRACT

An expansion/compression mechanism of a piston rod assembly is composed of a bush shaft, a first cylindrical piston rod that is screwed with the bush shaft, a second cylindrical piston rod that is screwed with the first piston rod, and a piston rod holding member for housing the bush shaft and these piston rods. Therefore, the piston rods move linearly in multiple stages.

3 Claims, 15 Drawing Sheets

(51) Int. Cl.
*A61M 5/31* (2006.01)
*A61M 5/24* (2006.01)

(52) U.S. Cl.
CPC .... *A61M 2205/581* (2013.01); *A61M 2205/583* (2013.01)

(56) References Cited

U.S. PATENT DOCUMENTS

| | | | |
|---|---|---|---|
| 4,718,576 A * | 1/1988 | Tamura et al. | 222/63 |
| 4,950,246 A * | 8/1990 | Muller | 604/154 |
| 5,338,310 A | 8/1994 | Lewandowski | |
| 5,628,309 A * | 5/1997 | Brown | 600/310 |
| 5,690,618 A * | 11/1997 | Smith et al. | 604/232 |
| 5,720,733 A * | 2/1998 | Brown | 604/207 |
| 5,779,675 A | 7/1998 | Reilly et al. | |
| 5,928,201 A * | 7/1999 | Poulsen et al. | 604/208 |
| 5,938,642 A * | 8/1999 | Burroughs et al. | 604/208 |
| 5,989,221 A | 11/1999 | Hjertman | |
| 6,171,276 B1 | 1/2001 | Lippe et al. | |
| 6,248,090 B1 * | 6/2001 | Jensen et al. | 604/67 |
| 6,277,098 B1 * | 8/2001 | Klitmose et al. | 604/207 |
| 6,514,230 B1 * | 2/2003 | Munk et al. | 604/207 |
| 6,607,512 B2 | 8/2003 | Oliver et al. | |
| 6,716,195 B2 | 4/2004 | Nolan et al. | |
| 7,150,741 B2 * | 12/2006 | Erickson et al. | 604/890.1 |
| 7,967,812 B2 * | 6/2011 | Jasperson et al. | 604/890.1 |
| 2001/0011163 A1 | 8/2001 | Nolan et al. | |
| 2004/0024361 A1 | 2/2004 | Fago et al. | |
| 2004/0030296 A1 * | 2/2004 | Langley et al. | 604/207 |
| 2005/0029277 A1 * | 2/2005 | Tachibana | 221/9 |
| 2005/0090781 A1 | 4/2005 | Baba et al. | |

FOREIGN PATENT DOCUMENTS

| | | |
|---|---|---|
| JP | 60-21449 | 2/1985 |
| JP | 4-95770 | 8/1992 |
| JP | 4-294776 | 10/1992 |
| JP | 5-337182 | 12/1993 |
| JP | 11-267207 | 10/1999 |
| JP | 11-511356 | 10/1999 |
| JP | 2000-296988 | 10/2000 |
| JP | 2000-513974 | 10/2000 |
| JP | 2001017542 | 1/2001 |
| JP | 3088706 | 7/2002 |
| JP | WO03/057286 | 7/2003 |
| WO | 97/00091 | 1/1997 |
| WO | 97/07841 | 3/1997 |
| WO | 98/01173 | 1/1998 |
| WO | 02/051477 | 7/2002 |
| WO | 03/024385 | 3/2003 |
| WO | 03/057286 | 7/2003 |

* cited by examiner

ADMINISTRATION APPARATUS FOR MEDICAL USE

This application is a divisional of application Ser. No. 11/071,466, filed Mar. 4, 2005, now abandoned.

FIELD OF THE INVENTION

The present invention relates to an administration apparatus for medical use which is driven by an electric driving source to perform administration of a drug and, more particularly, to an administration apparatus that facilitates replacement of drug cartridges.

BACKGROUND OF THE INVENTION

A patient addicted to insulin must get plural injections of insulin per week or day. A required amount of insulin varies from patient to patient. A required amount of insulin for each patient varies from injection to injection, and it also varies from day to day.

A patient who performs injection by himself attaches a drug cartridge containing a drug to an injector, and attaches a needle assembly to an elastic seal of the drug cartridge, and thereafter, sets a dose, and operates the injector to inject the drug into his body. The drug in the drug cartridge runs out when such administration is performed a few times. The patient detaches an empty drug cartridge from the injector, and attaches a new drug cartridge to repeat the above-mentioned injection. As for a conventional injector, when the drug cartridge is replaced with a new cartridge, a member that holds the drug cartridge (hereinafter referred to as a cartridge holder) is detached from a body of the injector, and the drug cartridge is detached from the cartridge holder. Then, a new drug cartridge is inserted into the cartridge holder, and thereafter, the cartridge holder is attached to the injector (for example, see Japanese Utility Model Registration No. 3088706).

Although the above-mentioned conventional injector is a hand-operated injector, there is a motor-operated injector as shown in FIG. 24. FIG. 24 is a diagram illustrating inner structure of a motor-operated injector which is currently popular for dental use. A principle of drug administration will be described with reference to FIG. 24. A syringe 203 filled with a drug is set in a cartridge holder 202 attached to a body 210.

When a switch SW1 is pressed, a motor 211 rotates forward, and a rotational force is decelerated by a deceleration gear box 209 that is directly connected to the motor 211, whereby a deceleration gear main shaft 208 of the deceleration gear box 209 is rotated. An end of the deceleration gear main shaft 208 is engaged with a gear 206 via a rotation plank 207, whereby the gear 206 is rotated. Further, since the gear 206 is engaged with a gear 205, a rotational force of the gear 206 propagates to the gear 205. A gear 205a is located coaxially with the gear 205 so as to be engaged with a rack 204a that is provided on a lower right half of an extrusion piston 204. When the gear 205 rotates, the gear 205a also rotates in the same direction as the gear 205, and consequently, the extrusion piston 204 moves toward an injection needle 213, whereby drug in the syringe 203 is pressed out of the injection needle 213.

During injection, after performing air releasing in the above-mentioned operation, the injection needle 213 is inserted into a target area, and the drug is administered. In FIG. 24, SW2 denotes a switch for rotating the motor 211 in a reverse order, and 212 denotes a battery for driving the motor 211.

Further, it is very important for an insulin injector to be portable, and therefore, a compact and light-weight injector is desired. The conventional injector is generally provided with a linear piston having a stroke that enables injection of all drug in the drug cartridge. However, there is an injector provided with a curvature type piston (for example, see Japanese Published Patent Application No. 2000-513974).

By the way, when a patient actually uses an injector, the patient desires easy replacement of drug cartridges.

In the conventional injector, however, the patient must detach the cartridge holder into which the drug cartridge is inserted from the body of the injector, detach the drug cartridge from the cartridge holder, attach a new drug cartridge to the holder, and mount the cartridge holder onto the injector body, resulting in an inconvenient and troublesome operation.

Further, in a case of the injector having a linear piston, the piston must have a stroke that enables injection of all drug in the drug cartridge, and a length of the piston becomes approximately equal to an entire length of the drug cartridge. Therefore, a length of the injector itself becomes at least two times as long as the drug cartridge, leading to an increase in a size of the injector. Further, in a case of the injector having a curvature type piston, a length of the injector becomes shorter than that of the linear piston rod. However, since the piston has a curvature, a thickness of the injector is increased, leading to a disadvantage in handleability.

Furthermore, in the conventional administration apparatus for medical use shown in FIG. 24, although operation is easy because drug injection is motor-operated, the patient might be anxious as to whether or not the motor-operated injector including a drive mechanism such as a motor is normally operated. An act of drug administration itself provides mental stress to the patient, and furthermore, abnormal operation of the motor-operated injector greatly affects a human body, which may endanger the life of the patient.

The conventional administration apparatus for medical use is constructed as described above, and operation of cartridge replacement is troublesome.

Further, a size of the apparatus is too large to handle.

Furthermore, as for the motor-operated apparatus, the patient might be anxious during drug administration about air releasing before injection, an operation state of a mechanism, or the like.

SUMMARY OF THE INVENTION

The present invention is made to solve the above-described problems and has for its object to provide an administration apparatus for medical use which enables a patient to easily replace cartridges, and minimizes a size of an injector itself.

It is another object of the present invention to provide an administration apparatus for medical use which eases physical and mental pains of a patient by detecting abnormal operation during injection and informing the same to a patient, thereby enabling the patient to perform administration of a drug with high stability.

Other objects and advantages of the invention will become apparent from a detailed description that follows. The detailed description and specific embodiments described are provided only for illustration since various additions and modifications within the scope of the invention will be apparent to those of skill in the art from the detailed description.

According to a first aspect of the present invention, an administration apparatus for medical use includes: a drug cartridge having an end closed with a plunger, and containing a drug inside; a cartridge holder for holding the drug cartridge; a needle holder which is provided at an end of the cartridge holder slidably in an axial direction of the cartridge holder, and is swingable with respect to the axial direction at its sliding end portion; and a needle assembly for inserting a needle into a target region, and administrating the drug that is ejected from another end of the drug cartridge by movement of a piston rod that presses the plunger in the drug cartridge, with the needle assembly being detachably provided on the needle holder, wherein the needle holder is slid in the axial direction of the cartridge holder as well as being swung with respect to the axial direction at its sliding end portion, thereby exposing a front end portion of the drug cartridge at a front end of the cartridge holder to detach the drug cartridge from the cartridge holder. Therefore, the drug cartridge can be detached or attached from/to the cartridge holder with the cartridge holder being held by the administration apparatus, thereby facilitating cartridge replacement.

According to a second aspect of the present invention, in the administration apparatus for medical use according to the first aspect, detaching of the drug cartridge is possible in a state where the needle assembly is attached to the needle holder. Therefore, handling is facilitated.

According to a third aspect of the present invention, in the administration apparatus for medical use according to the first aspect, the needle holder is provided with a lever for moving the drug cartridge toward the piston rod with an operation of attaching the needle assembly to the needle holder. Therefore, it is possible to check whether or not the needle assembly is attached by detecting a state of the lever.

According to a fourth aspect of the present invention, in the administration apparatus for medical use according to the first aspect, the cartridge holder is provided with a force-applying member for pushing the drug cartridge toward the needle holder. Therefore, it is possible to check whether or not the needle assembly and the drug cartridge are attached by detecting a position of a force-applying unit attached to the cartridge holder.

According to a fifth aspect of the present invention, in the administration apparatus for medical use according to the first aspect, when replacing the drug cartridge, the piston rod is moved back to its initial position with an operation of moving the needle holder toward a position where the needle assembly is attached. Therefore, the piston rod can be returned to the initial position when replacing the cartridge, leading to improved operability.

According to a sixth aspect of the present invention, the administration apparatus for medical use according to the first aspect further includes a movable target-region contact cover that covers a peripheral side surface of the needle holder, and only a needle of the needle assembly is exposed from the target-region contact cover when performing injection. Therefore, a periphery of the needle holder is covered with the target-region contact cover except when performing injection, thereby preventing a danger such that the needle is inserted by mistake.

According to a seventh aspect of the present invention, in the administration apparatus for medical use according to the sixth aspect, when replacing the drug cartridge, the target-region contact cover is moved to a position where the needle holder is exposed. Therefore, a user can easily touch the needle holder when replacing the drug cartridge, leading to improved operability.

According to an eighth aspect of the present invention, the administration apparatus for medical use according to the sixth aspect further includes a unit for detecting a position of the target-region contact cover. Therefore, an accident such that the needle is inserted by mistake during use can be effectively avoided.

According to a ninth aspect of the present invention, an administration apparatus for medical use includes: a drug cartridge having an end closed with a plunger, and containing a drug inside; a cartridge holder for holding the drug cartridge; and a piston rod assembly having plural stages of expansion/compression mechanisms, and pushing the plunger in the drug cartridge to move the plunger. Since motion of the piston rod is linear in plural stages, a size of the apparatus is significantly reduced, thereby providing an administration apparatus for medical use having excellent portability.

According to a tenth aspect of the present invention, in the administration apparatus for medical use according to the ninth aspect, the plural stages of expansion/compression mechanisms of the piston rod assembly have plural stages of piston rods which are linearly slidable in parallel to an axial direction of the cartridge holder, and a length of each piston rod is shorter than an entire length of the drug cartridge. Since motions of the piston rods are linear in plural stages, a size of the apparatus is significantly reduced, thereby providing an administration apparatus for medical use having excellent portability.

According to an eleventh aspect of the present invention, in the administration apparatus for medical use according to the tenth aspect, the plural piston rods are concentrically arranged, and the piston rods are successively slid from a piston rod that is positioned at an outermost concentric circle. Since motions of the piston rods are linear in plural stages, a size of the apparatus is significantly reduced, thereby providing an administration apparatus for medical use having excellent portability.

According to a twelfth aspect of the present invention, an administration apparatus for medical use which performs administration of a drug using an electric driving source, comprises: a drug cartridge having an end closed with a plunger, and containing a drug inside; a cartridge holder for holding the drug cartridge; a piston rod for pressing the plunger held in the drug cartridge to move the plunger; a needle assembly for inserting a needle into a target region, and administering the drug that is emitted from another end of the drug cartridge with movement of the piston rod; and a control circuit for controlling an air releasing operation for the drug cartridge and/or the injection needle so that the air releasing operation is performed at a speed lower than a speed of drug administration. Therefore, it is possible to reduce a risk of the drug adhered to the injection needle or the like being splattered when a user visually checks air releasing, and reduce mental pain due to administration.

According to a thirteenth aspect of the present invention, in the administration apparatus for medical use according to the twelfth aspect, the air releasing operation is performed with movement of the piston rod. Therefore, the air releasing operation is facilitated.

According to a fourteenth aspect of the present invention, in the administration apparatus for medical use according to the thirteenth aspect, during the air releasing operation, the piston rod is moved at a speed lower than a speed of the piston rod during drug administration. Therefore, it is possible to reduce a risk of the drug adhered to the injection needle or the like being splattered when the user visually checks air releasing, and reduce mental pain due to administration.

According to a fifteenth aspect of the present invention, in the administration apparatus for medical use according to the fourteenth aspect, such low-speed operation of the piston rod during the air releasing operation is performed by PWM (Pulse Width Modulation) control for controlling the piston rod with an ON-OFF ratio of a pulse width being varied. Therefore, it is possible to reduce a risk of the drug adhered to the injection needle or the like being splattered when the user visually checks air releasing, and reduce mental pain due to administration.

According to a sixteenth aspect of the present invention, in the administration apparatus for medical use according to the fourteenth aspect, such low-speed operation of the piston rod during the air releasing operation is performed by voltage control. Therefore, it is possible to reduce a risk of the drug adhered to the injection needle or the like being splattered when the user visually checks air releasing, and reduce mental pain due to administration.

According to a seventeenth aspect of the present invention, an administration apparatus for medical use which performs administration of a drug using an electric driving source, comprises: a drug cartridge having an end closed with a plunger, and containing a drug inside; a cartridge holder for holding the drug cartridge; a piston rod for pressing the plunger in the drug cartridge to move the plunger; a needle assembly for inserting a needle into a target region, and administering the drug that is emitted from another end of the drug cartridge with movement of the piston rod; and a control circuit for performing control so that an air releasing operation for the drug cartridge and/or the injection needle is always performed before performing a drug administration operation. Therefore, air releasing is always performed before drug administration, whereby mental anxiety to a user can be reduced.

According to an eighteenth aspect of the present invention, the administration apparatus for medical use according to the seventeenth aspect further includes an air releasing switch for performing the air releasing operation, and an administration switch for injecting the drug, and the control circuit permits an operation by turn-on of the administration switch after the air releasing operation. Therefore, there is no fear of drug administration when air releasing is not performed, whereby mental anxiety to a user can be reduced.

According to a nineteenth aspect of the present invention, the administration apparatus for medical use according to the twelfth or seventeenth aspect further includes a contact sensor for detecting whether or not a portion of the administration apparatus in the vicinity of the needle assembly contacts a target region, and the air releasing operation is suppressed when the contact sensor contacts the target region. Therefore, it is possible to prevent an accident such that the needle is inserted into the human body during air releasing, whereby mental anxiety to the user can be reduced.

According to a twentieth aspect of the present invention, an administration apparatus for medical use which performs administration of a drug using an electric driving source, comprises: a drug cartridge having an end closed with a plunger, and containing a drug inside; a cartridge holder for holding the drug cartridge; a piston rod for pressing the plunger in the drug cartridge to move the plunger; a needle assembly for inserting a needle into a target region, and administering the drug that is emitted from another end of the drug cartridge with movement of the piston rod; a dose setting circuit for setting, by a user, a dose of drug to be administered; a dose holding circuit for holding doses of drug which have been administered in the past; a dose comparison circuit for comparing a dose that is set by the dose setting circuit with doses that are held in the dose holding circuit; and a control circuit for performing control so as to suppress operation of the piston rod when a result of this comparison by the dose comparison circuit is equal to or larger than a predetermined value. Therefore, the user cannot proceed to an administration step when the dose changes significantly, thereby reducing mental and physical pains caused by use of the motor-operated administration apparatus for medical use.

According to a twenty-first aspect of the present invention, in the administration apparatus for medical use according to the twentieth aspect, the dose holding circuit holds a dose of drug that has been administered most recently, and the dose comparison circuit compares a dose that is set by the user with the dose that has been administered most recently. Therefore, the user cannot proceed to the administration step when the dose changes significantly, thereby reducing mental and physical pains caused by use of the motor-operated administration apparatus for medical use.

According to a twenty-second aspect of the present invention, in the administration apparatus for medical use according to the twentieth aspect, the dose holding circuit holds doses of drug of plural times of administrations performed in the past, and the dose comparison circuit compares a dose that is set by the user with a dose that is obtained on basis of the plural times of administrations performed in the past. Therefore, the user cannot proceed to the administration step when the dose changes significantly, thereby reducing mental and physical pains caused by use of the motor-operated administration apparatus for medical use.

According to a twenty-third aspect of the present invention, in the administration apparatus for medical use according to the twenty-second aspect, the dose obtained on the basis of the plural times of administrations performed in the past is an average of doses of the plural times of administrations in the past. Therefore, the user cannot proceed to the administration step when the dose changes significantly, thereby reducing mental and physical pains caused by use of the motor-operated administration apparatus for medical use.

According to a twenty-fourth aspect of the present invention, the administration apparatus for medical use according to the twentieth aspect further includes a notification unit for notifying the user that administration is not possible, when the result of comparison by the dose comparison circuit is equal to or larger than the predetermined value. When the dose changes significantly, it is informed to the user and then the user confirms the dose, thereby reducing mental and physical pains caused by use of the motor-operated administration apparatus for medical use.

According to a twenty-fifth aspect of the present invention, in the administration apparatus for medical use according to the twenty-fourth aspect, when the user permits administration of the dose of drug that is set by the user after the user is notified that administration is not possible using the notification unit, the control circuit cancels restriction on operation of the piston rod. Therefore, even when the dose changes significantly, the user can perform administration for his own convenience. Since this dose change is informed to the user before administration and then the user can check the dose, mental and physical pains caused by use of the motor-operated administration apparatus for medical use can be reduced.

According to a twenty-sixth aspect of the present invention, an administration apparatus for medical use which performs administration of a drug using an electric driving source, comprises: a drug cartridge having an end closed with a plunger, and containing a drug inside; a cartridge holder for holding the drug cartridge; a piston rod for pressing the plunger held in the drug cartridge to move the plunger; a needle assembly for inserting a needle into a target region, and administering the drug that is emitted from another end of the drug cartridge with movement of the piston rod; a dose setting circuit for setting, by a user, a dose of drug to be administered; a dose detection circuit for detecting an actual dose of drug using an electronic circuit; and a comparison detection circuit for comparing a dose that is set by the dose setting circuit with a result of detection by the dose detection circuit to detect overdose or underdose of the drug. Therefore, it is possible to monitor an actual dose of drug by the electronic circuit as well as to monitor a dose of drug by the program for setting the dose in advance, and injection of overdose or underdose of the drug can be prevented by forced stoppage or the like even when a program is operated abnormally, thereby reducing mental and physical pains caused by use of the motor-operated administration apparatus.

According to a twenty-seventh aspect of the present invention, in the administration apparatus for medical use according to the twenty-sixth aspect, the comparison detection circuit stops the piston rod when it detects overdose of the drug, thereby to stop administration. Therefore, it is possible to prevent overdose of drug even when a program is abnormally operated, reducing mental and physical pains caused by use of the motor-operated administration apparatus for medical use.

According to a twenty-eighth aspect of the present invention, in the administration apparatus for medical use according to the twenty-sixth aspect, the dose detection circuit detects the dose on basis of an amount of movement of the piston rod. Therefore, an actual dose of drug can be detected by the electronic circuit.

According to a twenty-ninth aspect of the present invention, in the administration apparatus for medical use according to the twenty-sixth aspect, the dose detection circuit detects the dose on basis of a time when the piston rod moves at a constant speed. Therefore, an actual dose of drug can be detected by the electronic circuit.

DETAILED DESCRIPTION OF THE PREFERRED EMBODIMENTS

Embodiment 1

Figure 1:
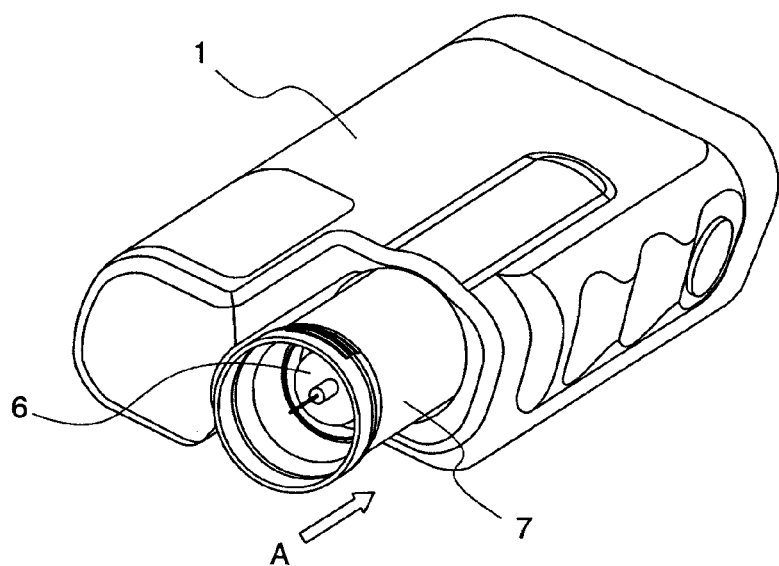
FIG. 1 is a perspective view illustrating an entirety of an administration apparatus for medical use according to a first embodiment of the present invention.

FIG. 1 is a diagram illustrating an entire construction of an administration apparatus for medical use according to a first embodiment of the present invention.

In FIG. 1, reference numeral 1 denotes an administration apparatus having, at an end thereof, a target-region contact cover 7 to be applied to a target region of a patient's body to be subjected to injection when the patient performs administration by himself, and a needle assembly 6 is housed in the cover 7.

Further, a drug cartridge containing a drug, an end of which is closed with a plunger (not shown), is inserted in the administration apparatus. When the needle assembly 6 pierces the target region, a piston rod (not shown) that presses the plunger moves, whereby the drug emitted from an end of the drug cartridge is injected into the patient's body.

Figure 2:
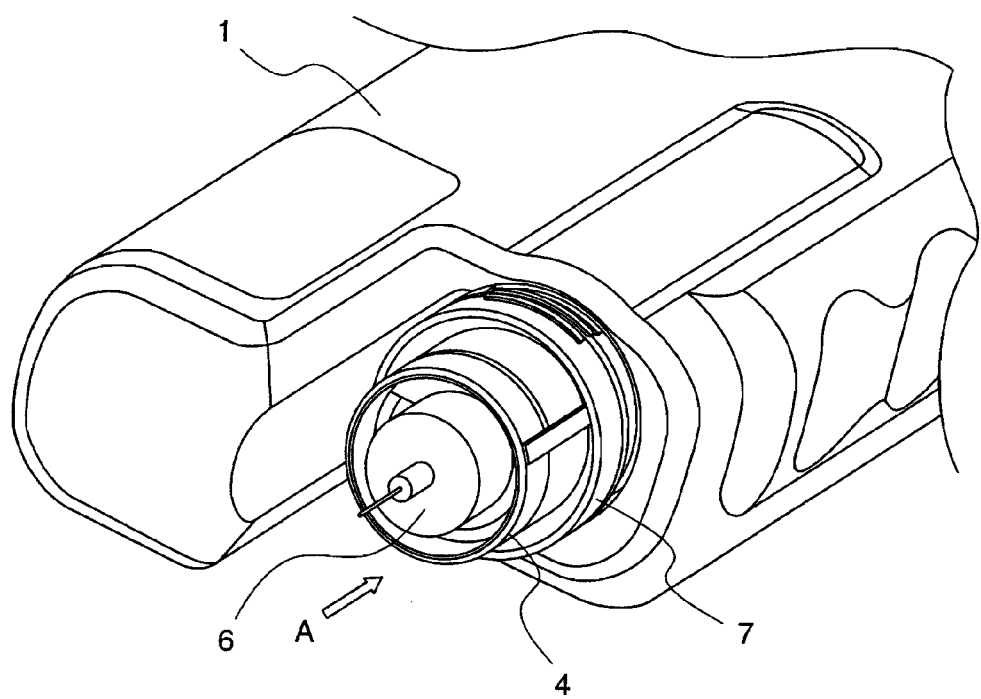
FIG. 2 is a diagram illustrating a part of the administration apparatus in the vicinity of a needle holder, for explaining replacement of drug cartridges.

When the patient replaces the drug cartridge, the target-region contact cover 7 is slid in a direction of arrow A as shown in FIG. 2, whereby the needle assembly 6 attached to a needle holder 4 is exposed. Usually, cartridge replacement should be performed after a protection cover (not shown) is put on the needle assembly 6 to avoid an accident of error insertion of the needle assembly 6. However, description of the protection cover is omitted.

Figure 3:
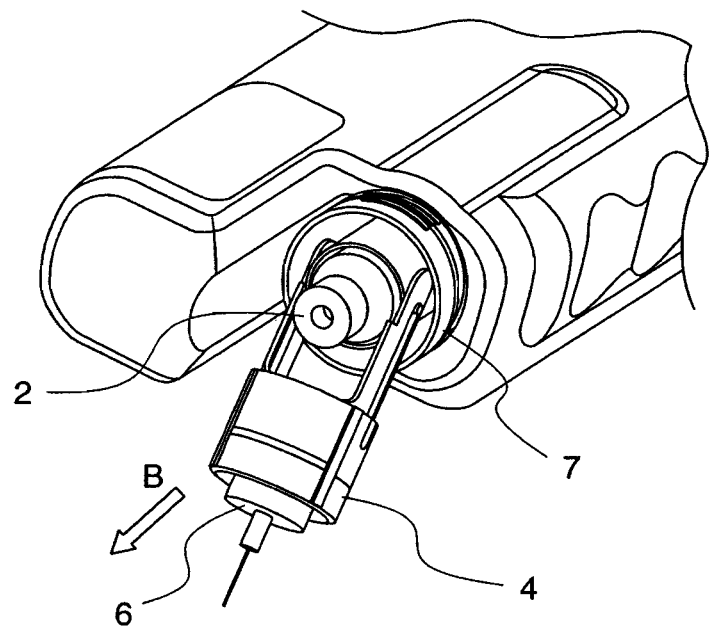
FIG. 3 is a diagram illustrating a state where the needle holder is drawn from a body of the administration apparatus, for explaining replacement of drug cartridges.
Figure 4:
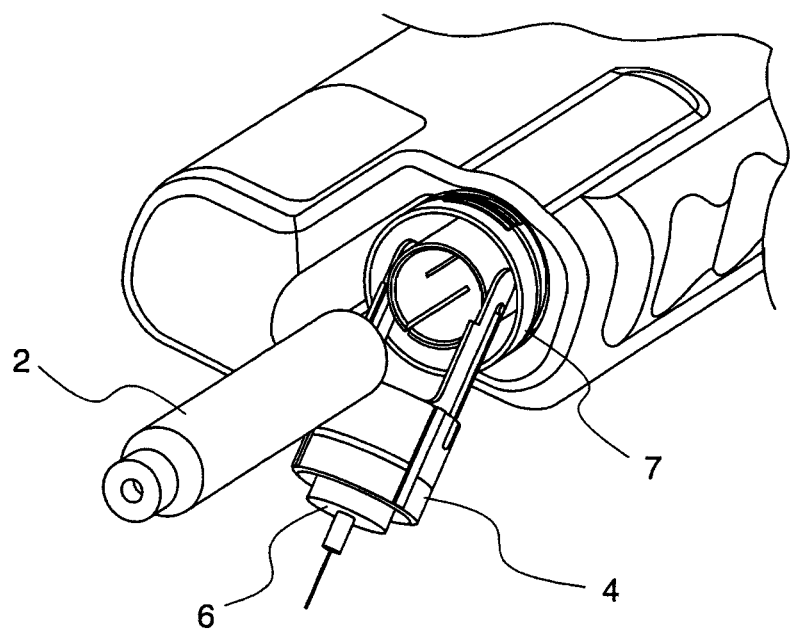
FIG. 4 is a diagram illustrating a state where the drug cartridge is detached from the body, for explaining replacement of drug cartridges.

Next, as shown in FIG. 3, the needle holder 4 is slid in a direction of arrow B. The needle holder 4 is moved up to a predetermined position, and then the needle holder 4 is swung about a shaft (not shown), whereby the drug cartridge 2 is exposed from the administration apparatus 1. Thereafter, the patient detaches the drug cartridge 2.

An outline of cartridge replacement is as described above. Hereinafter it will be described in more detail using FIGS. 5 to 7.

Figure 5:
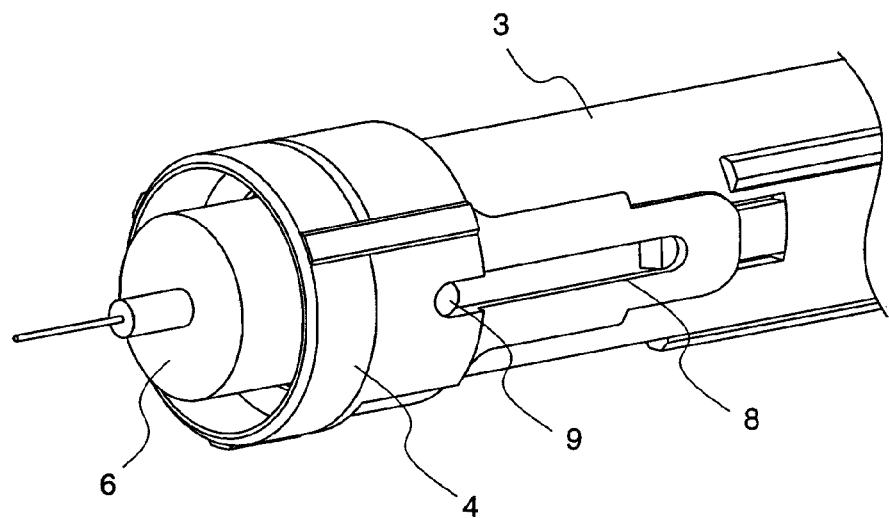
FIG. 5 is an enlarge view of a main part of the needle holder in the administration apparatus for medical use.

In FIG. 5, support struts 9 are provided on both sides of a front end of the cartridge holder 3 which holds the drug cartridge 2. Further, the needle holder 4 to which the needle assembly 6 is attached has grooves 8 for slide-guiding the support struts 9, and the needle holder 4 and the cartridge holder 3 are joined to each other by respective grooves 8 and support struts 9.

Figure 6:
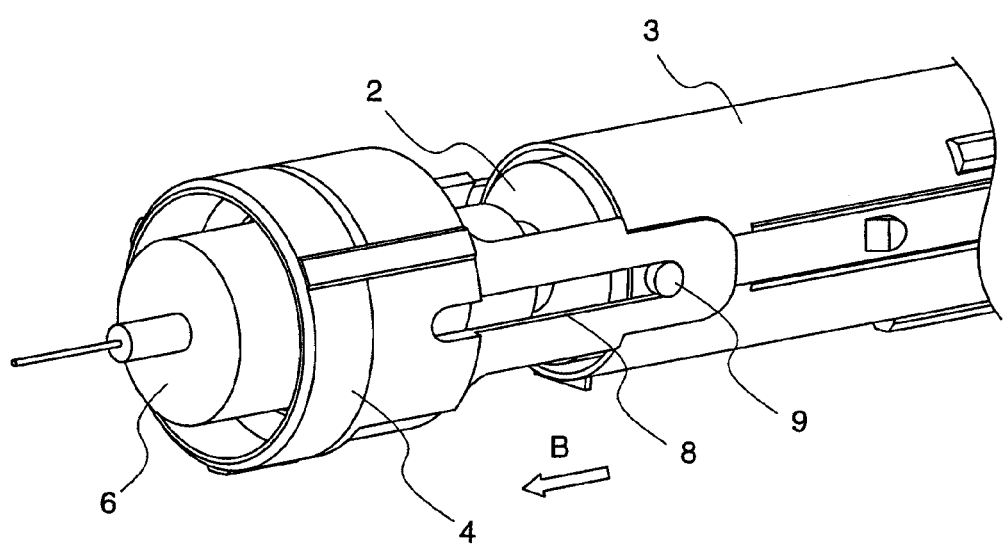
FIG. 6 is an enlarge view of a main part of the needle holder for explaining operation of the needle holder.
Figure 7:
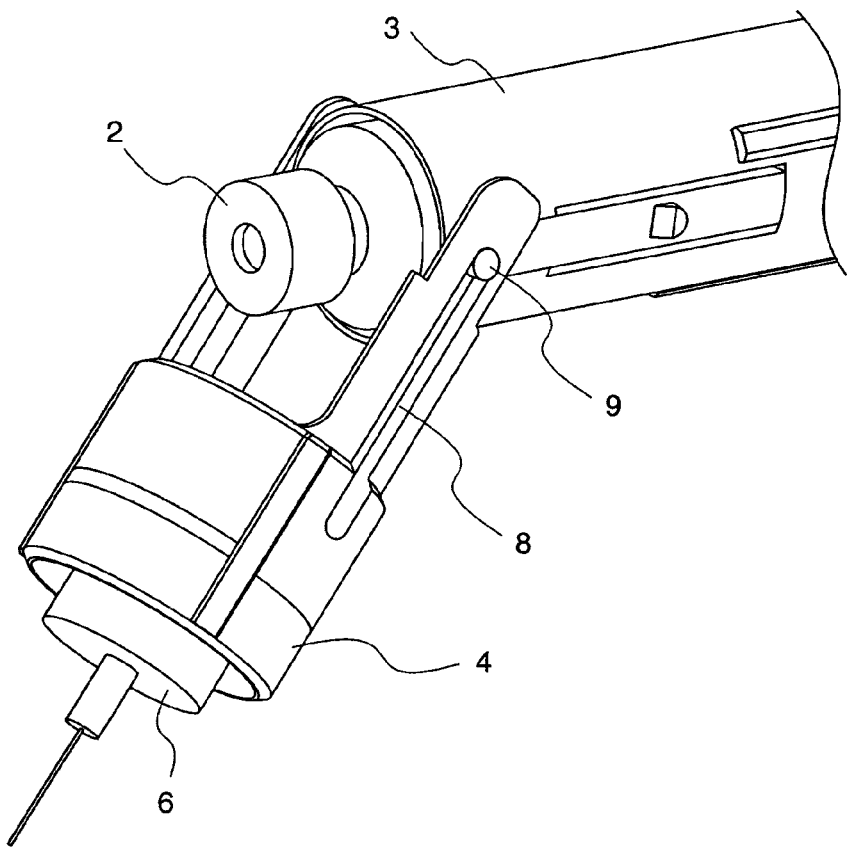
FIG. 7 is a diagram illustrating a state where the needle holder is slid, for explaining operation of the needle holder.

When the patient replaces the drug cartridge 2, as shown in FIG. 6, the target-portion contact cover 7 (refer to FIG. 2) is moved up to a predetermined position, and the needle holder 4 is slid in the direction of arrow B until a rear portion of the groove 8 contacts support strut 9. When the needle holder 4 reaches the predetermined position, the needle holder 4 swings about the support strut 9 as shown in FIG. 7, and a front end 2a of the drug cartridge 2 is exposed at the front end of the cartridge holder 3.

Thereafter, replacement of the drug cartridge 2 can be performed. After a new drug cartridge 2 is attached, the administration apparatus 1 is set in an injection-ready state by performing a reverse of the above-mentioned operation.

Further, during injection, only the needle portion of the needle assembly is exposed out of the contact cover. Therefore, at all other times, a periphery of the needle holder is covered, thereby preventing an accident such as needle insertion by mistake.

Further, a device for detecting a position of the contact cover may be provided to prevent an accident such as needle insertion by mistake during use. To be specific, the contact cover is detected by a position detection device that is provided in the administration apparatus when the contact cover is in a used position.

Figure 8:
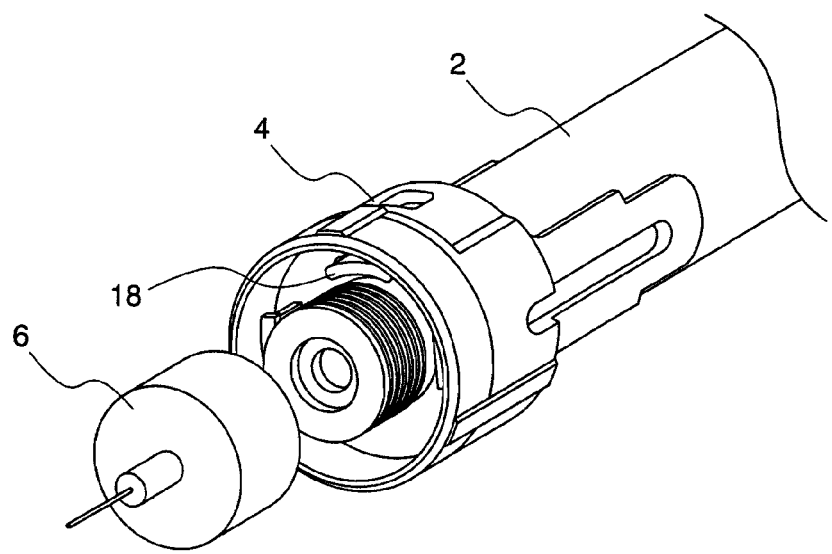
FIG. 8 is a diagram illustrating a piston rod assembly of the administration apparatus for medical use.
Figure 9:
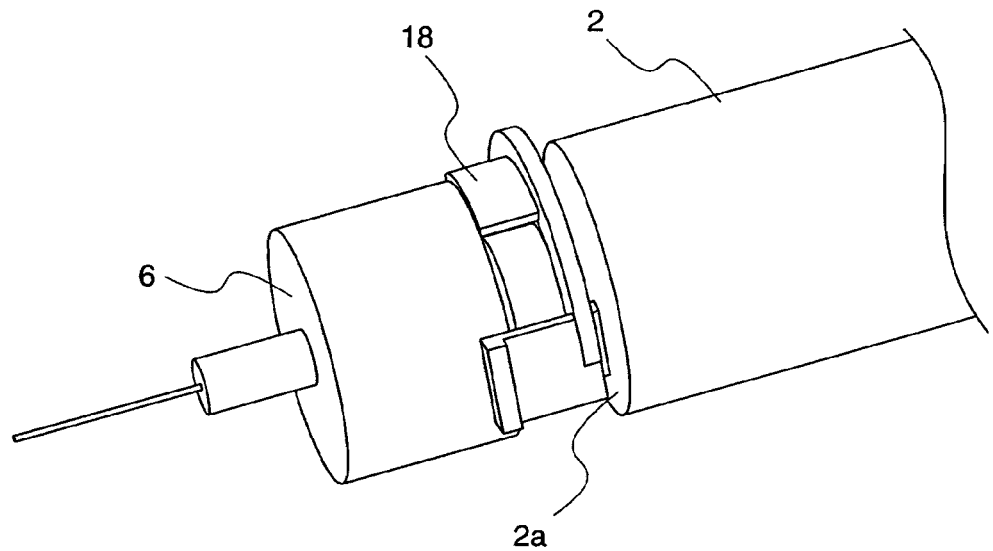
FIG. 9 is a diagram for explaining a state of a detection lever when attaching a needle assembly onto the needle holder of the administration apparatus.
Figure 10:
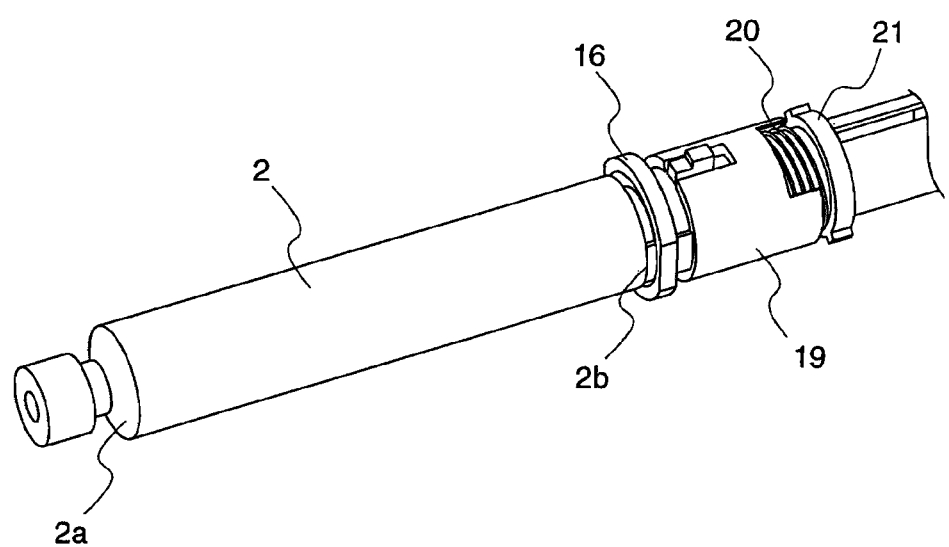
FIG. 10 is a diagram illustrating construction of a part of the administration apparatus in the vicinity of a rear end of the drug cartridge.

Next, a drug cartridge holding state will be described with reference to FIGS. 8 to 10.

A detection lever 18 is attached to the needle holder 4. FIG. 9 shows a state of the detection lever 18 in a case where the needle assembly 6 is attached to the needle holder 4 (refer to FIG. 8). When the needle assembly 6 is attached to the needle holder 4, a rear end portion of the needle assembly 6 presses the detection lever 18, and a rear end portion of the detection lever 18 presses the front end portion 2a of the drug cartridge 2. Further, as shown in FIG. 10, a rear end portion 2b of the drug cartridge 2 is pressed by a press member 19 that is slidably attached to a periphery of a piston rod hold member 16.

The press member 19 comprises a spring member 20 and a stopper member 21.

In the above-mentioned construction, presence/absence of the needle assembly 6 and the drug cartridge 2 can be detected by detecting a position of the press member 19.

Further, when replacing the drug cartridge, the needle holder 4 is moved in a direction in which the needle assembly 6 is attached, by the detection lever 18 and the piston rod holding member 16, whereby the piston rod is moved back to an initial position. Thus, operability during cartridge replacement is improved.

As described above, in the first embodiment of the present invention, since the front end of the drug cartridge 2 is exposed by drawing the needle holder 4 from a body of the administration apparatus 1 and swinging the holder 4, the drug cartridge 2 is detachable with the cartridge holder 3 being held by the administration apparatus 1. Therefore, in contrast to the conventional administration apparatus, the patient is free from a burden that the patient must separate the cartridge holder from the administration apparatus body every time the patient replaces the cartridge. Further, the patient can arbitrarily perform replacement of the drug cartridge regardless of a needle assembly attachment state, thereby facilitating handling.

The administration apparatus for medical use according to the present invention is applicable to both of a hand operated administration apparatus and a motor-operated administration apparatus.

Embodiment 2

Figure 11:
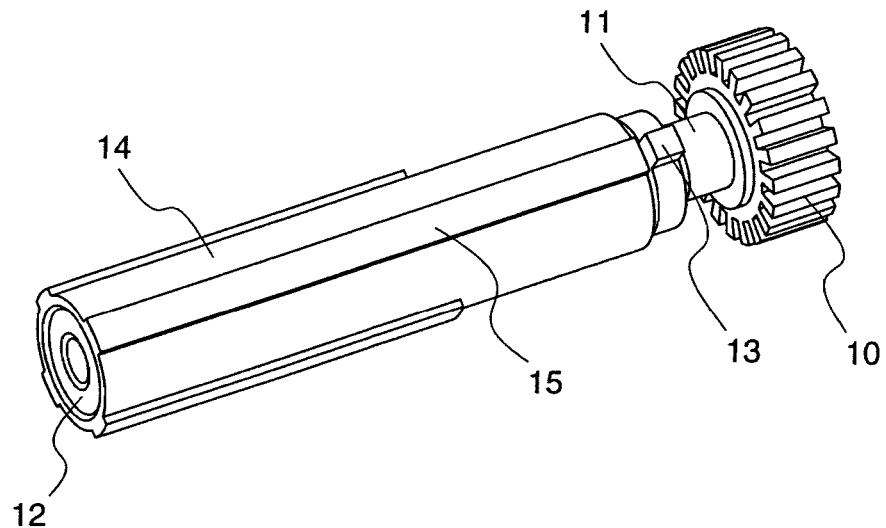
FIG. 11 is a diagram illustrating construction of a main part of a piston rod assembly of an administration apparatus for medical use according to a second embodiment of the present invention.
Figure 15:
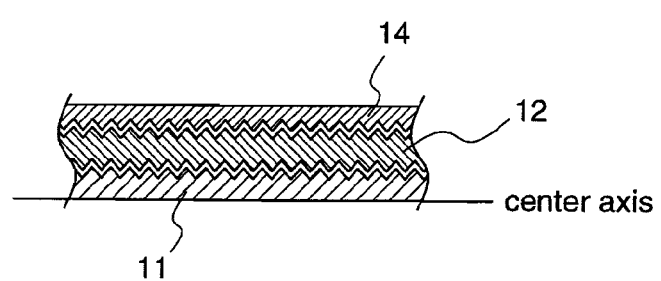
FIG. 15 is a cross-sectional view for explaining engagements of a bush shaft and respective piston rods of the administration apparatus according to the first embodiment.

Next, an administration apparatus for medical use according to a second embodiment of the present invention will be described. FIG. 11 is a diagram illustrating a piston rod assembly of a motor-operated administration apparatus for medical use according to the second embodiment of the present invention. As shown in FIG. 11, a bush shaft 11 having a length approximately equal to an entire length of the rod assembly and having a male thread (not shown) on its periphery is pushed into a driving gear 10 for transferring a driving power from a motor or the like (not shown). Further, a hollow piston rod 12 having, on its inner periphery, a female thread (not shown) that is screwed with the male thread of the bush shaft 11 has a male thread (not shown) on its periphery. Furthermore, a piston rod 14 having, on its inner periphery, a female thread (not shown) that is screwed with the piston rod 12 is screwed with the piston rod 12. How the bush shaft 11, the piston rod 12, and the piston rod 14 are screwed is shown in FIG. 15.

Figure 12:
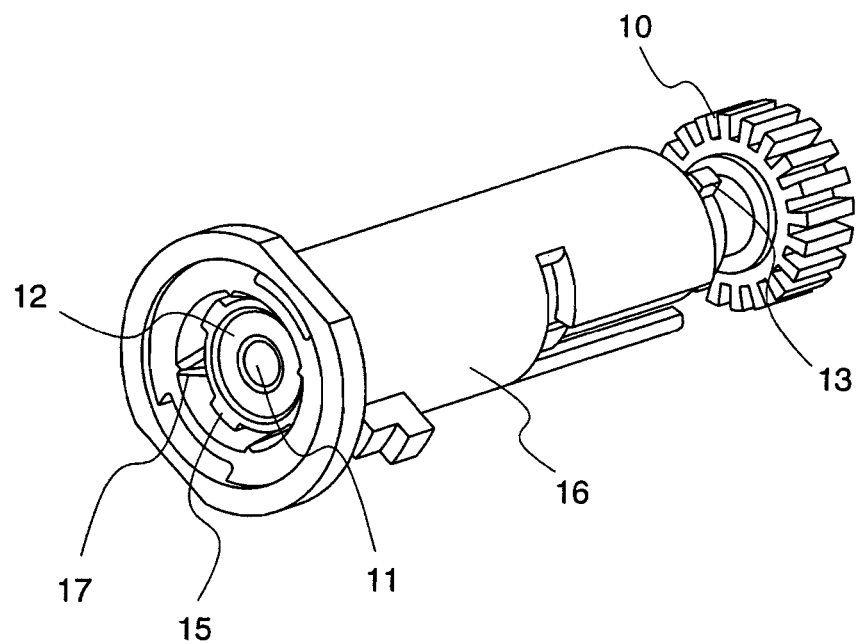
FIG. 12 is a diagram illustrating a state where the piston rod assembly of the administration apparatus according to the second embodiment is housed in a piston rod holding member.

Further, the piston rod 12 and the piston rod 14 are provided with convex-shaped rotation prevention parts 13 and 15, respectively. Further, as shown in FIG. 12, the piston rod 14 is covered with a hollow piston rod holding member 16 that allows the piston rod 14 to slide smoothly. Further, a concave-shaped piston rod rotation prevention part 17 which contacts the rotation prevention parts 13 and 15 of the piston rod 12 and the piston rod 14 to prevent the piston rods 12 and 14 from rotating, respectively, is provided in the piston rod holding member 16.

Next, actual operation will be described with reference to FIGS. 12 to 14. First of all, FIG. 12 shows an initial state, wherein the rotation prevention part 13 of the piston rod 12 is positioned outside the piston rod holding member 16. A driving force of the driving gear 10 is transferred to the bush shaft 11 and the piston rod 12, and the driving gear 10, the bush shaft 11, and the piston rod 12 rotate in one direction in synchronization with each other.

Figure 13:
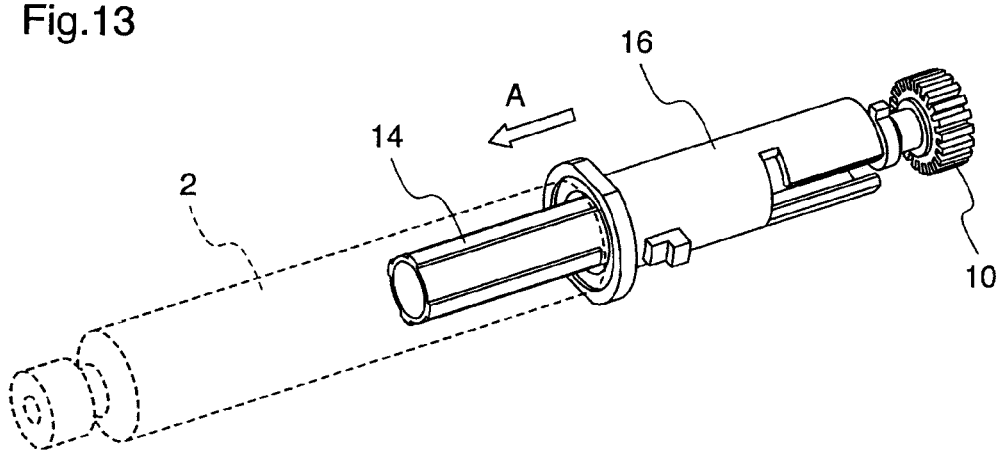
FIG. 13 is a diagram for explaining operation of the piston rod assembly of the administration apparatus according to the second embodiment.
Figure 14:
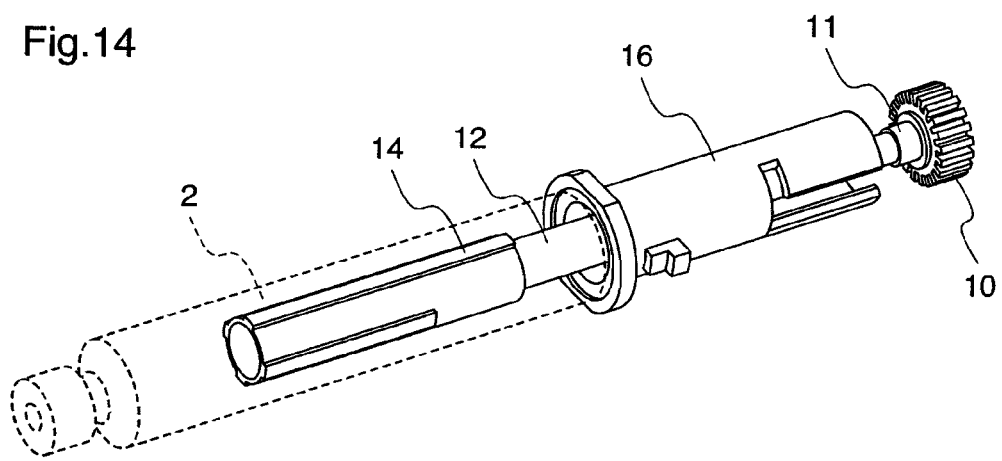
FIG. 14 is a diagram for explaining operation of the piston rod assembly of the administration apparatus according to the second embodiment.

Further, since the rotation prevention part 15 of the piston rod 14 cannot rotate because it contacts the piston rod rotation prevention part 17 of the piston rod holding member 16, a rotational force transferred from the piston rod 12 to the piston rod 14 is converted into a driving force for moving the piston rod 14 forward, whereby the piston rod 14 slides in a direction of arrow A as shown in FIG. 13. The male thread on the periphery of the piston rod 12 is not formed over its entire length, but a portion of a few millimeters from an opposite side of the rotation prevention part 13 is an imperfect thread portion. Accordingly, rotation of the piston rod 12 stops when an imperfect thread of the piston rod 12 reaches the thread of the piston rod 14.

Since the rotation prevention part 15 of the piston rod 14 still contacts the piston rod rotation prevention part 17 of the piston rod holding member 16, the piston rod 12 that has stopped rotation slides in the direction of arrow A in synchronization with the piston rod 14. Further, an instant when the rotation prevention part 15 of the piston rod 14 is apart from the piston rod rotation prevention part 17 of the piston holding member 16, the rotation prevention part 13 of the piston rod 12 contacts the piston rotation prevention part 17 of the piston holding member 16, and therefore, the piston rod 14 slides in the drug cartridge 2 in synchronization with sliding of the piston rod 12 (refer to FIG. 14). Then, the plunger of the drug cartridge 2 is pressed, whereby a drug is drained. The piston rod can be returned to the initial state by performing a reverse of the above-mentioned processing.

As described above, in the administration apparatus for medical use according to the second embodiment, an expansion/compression mechanism of the piston rod assembly is composed of the bush shaft 11, the cylindrical piston rod 12 that is screwed with the bush shaft 11, the cylindrical piston rod 14 that is screwed with the piston rod 12, and the piston rod holding member 16 that stores these piston rods, whereby motion of the piston rods is expanded linearly in plural stages to make the apparatus very compact, resulting in an administration apparatus for medical use having excellent portability.

While in this second embodiment a motor-operated administration apparatus for medical use has been described, the present invention is not restricted thereto. For example, a hand-operated administration apparatus for medical use which manually drives a driving gear 10 using a spring or the like is also within the scope of the present invention.

Embodiment 3

Next, an administration apparatus for medical use according to a third embodiment of the present invention will be described with reference to FIGS. 16 to 19.

Figure 16:
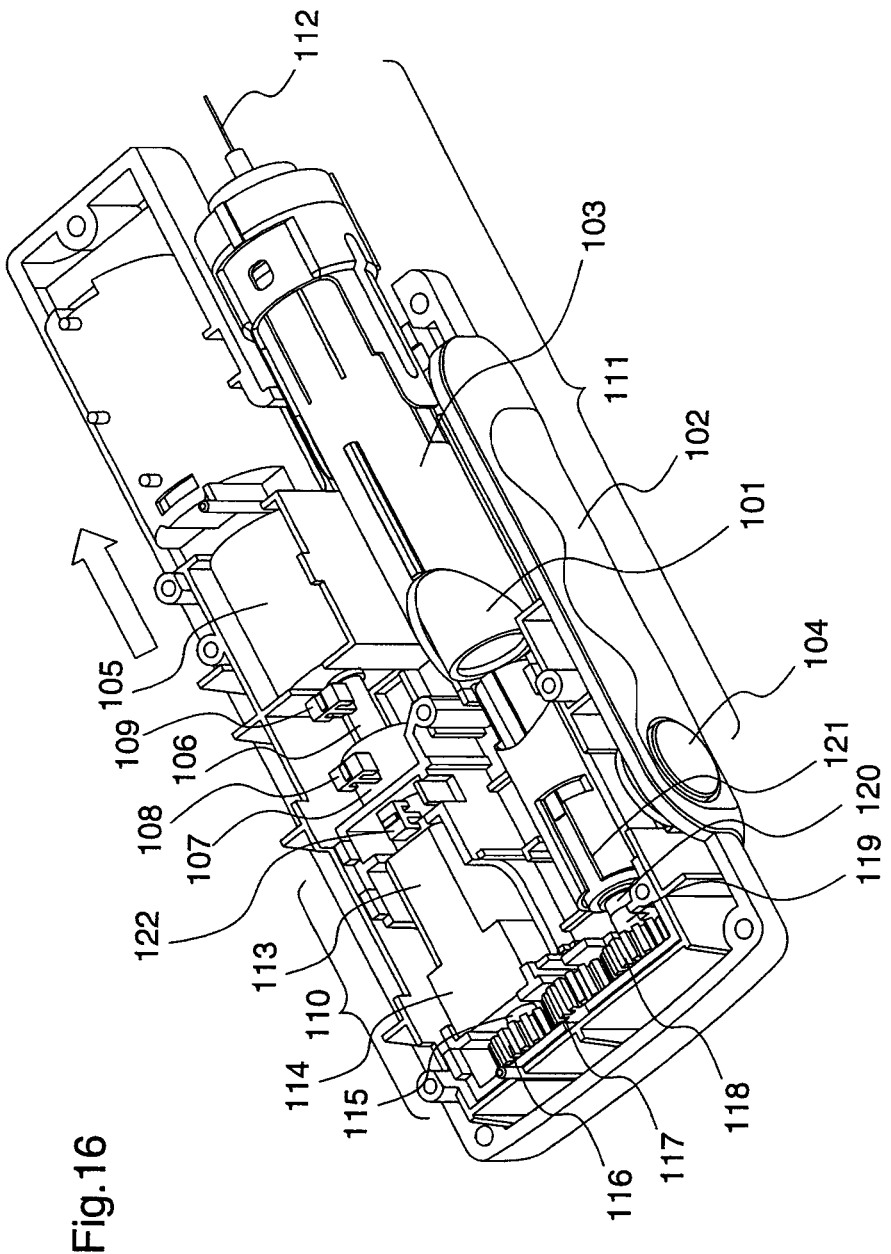
FIG. 16 is a perspective view illustrating internal structure of an administration apparatus for medical use according to a third embodiment of the present invention.
Figure 17:
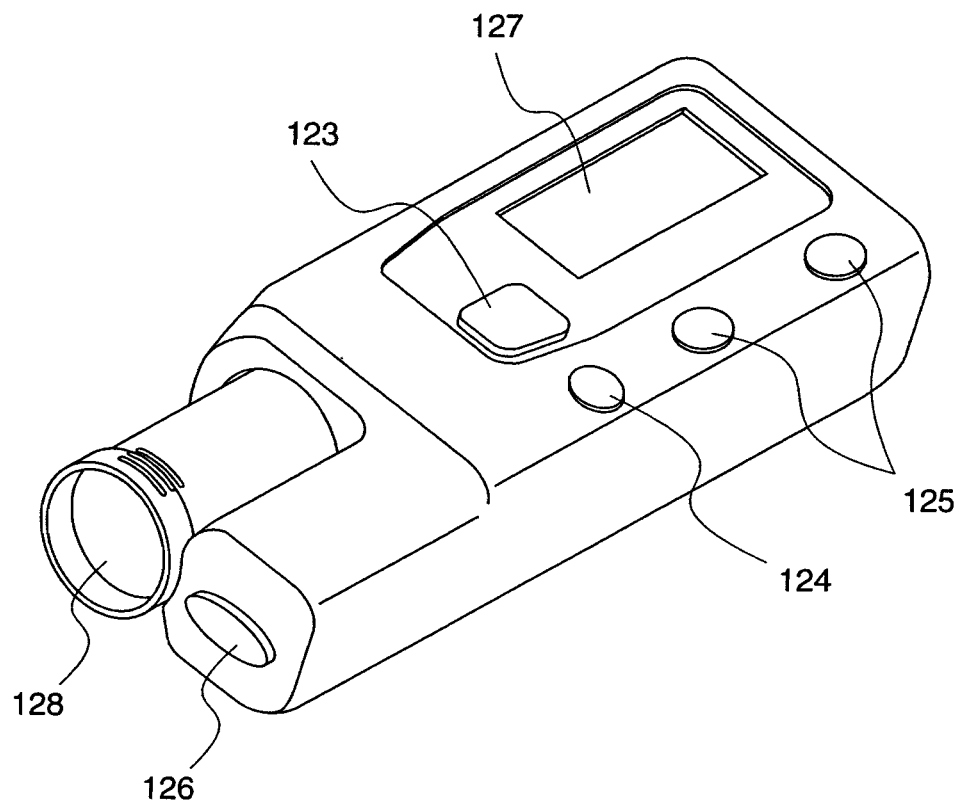
FIG. 17 is a perspective view illustrating an external appearance of the administration apparatus according to the third embodiment.
Figure 18:
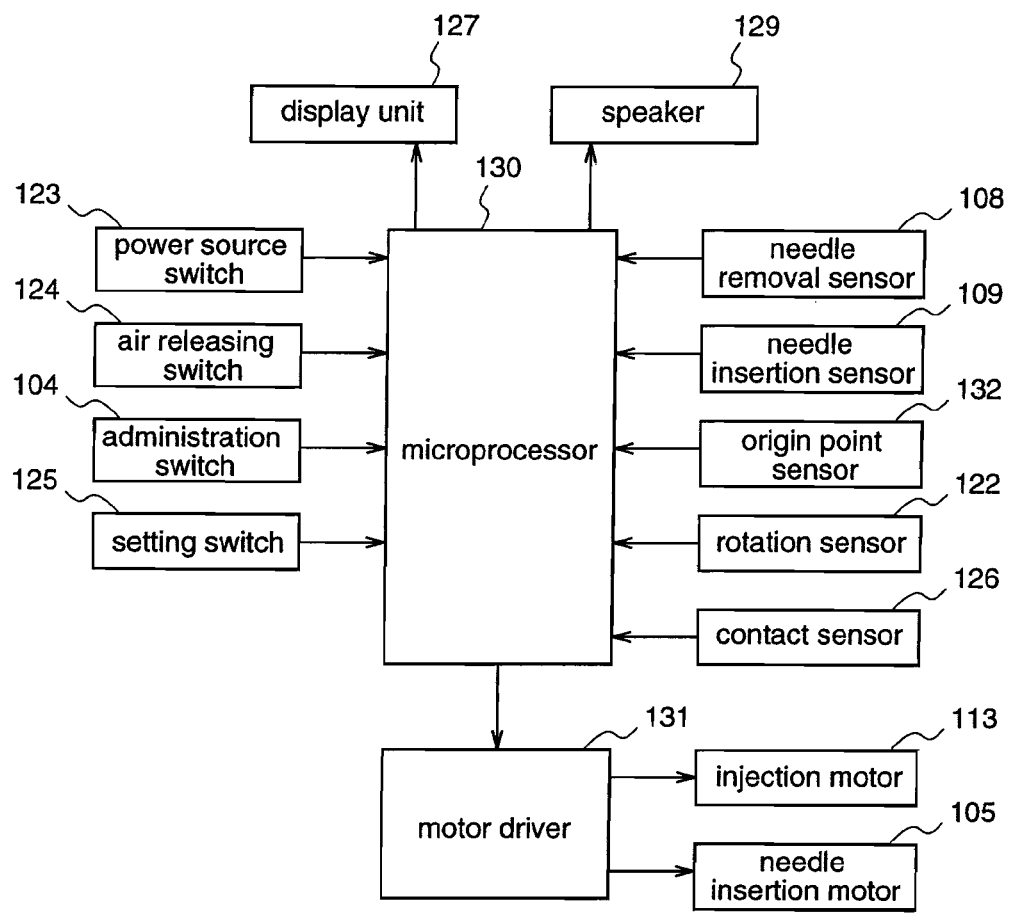
FIG. 18 is a block diagram for explaining connections of components in the administration apparatus according to the third embodiment as an electric circuit.
Figure 19:
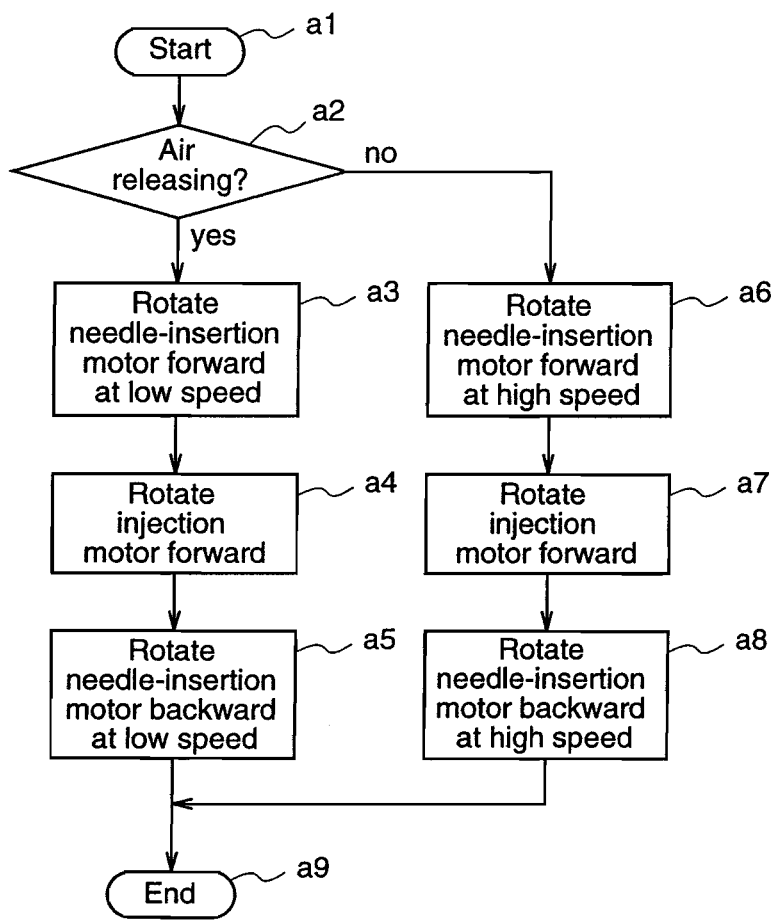
FIG. 19 is a flowchart for explaining operation of the administration apparatus according to the third embodiment.

FIG. 16 is a perspective view for explaining internal structure of an administration apparatus for medical use according to the third embodiment, FIG. 17 is a perspective view illustrating an external appearance of the administration apparatus, FIG. 18 is a block diagram for explaining connections in the administration apparatus as an electric circuit, and FIG. 19 is a flowchart for explaining operation of the administration apparatus.

Initially, FIG. 16 will be described.

FIG. 16 is a diagram illustrating construction of a motor-operated administration apparatus for medical use which performs an operation of administrating a drug using an electric driving source.

In FIG. 16, a syringe (drug cartridge) 101 filled with a drug is set in a cartridge holder 103 that is attached to a body 102 of the apparatus.

A user holds the body 102 with his hand, presses a contact sensor against a region to which the drug should be administered, and pushes an administration switch 104 that is provided on a side surface of the body 102. Then, a needle-insertion motor 105 rotates forward, and this rotational force propagates to a slide cap 107 through a slide rod 106 that is directly connected to the needle-insertion motor 105. The rotational force of the needle-insertion motor 105 is converted into a force of linear motion by the slide cap 107. The slide cap 107 moves in a direction of the arrow when the needle-insertion motor 105 rotates forward. A needle-removal sensor is turned off as the slide cap 107 starts to move. The slide cap 107 moves by a predetermined amount in the direction of the arrow. At this time, a needle-insertion sensor 109 is turned on, and rotation of the needle-insertion motor 105 stops.

The slide cap 107 is coupled to an inner frame assembly part 110. When the needle-insertion motor 105 rotates forward, the inner frame assembly part 110 moves in the direction of the arrow. The inner frame assembly part 110 is coupled to an injection assembly part 111. The injection assembly part 111 moves in the direction of the arrow when the needle-insertion motor 105 rotates forward, and inserts an injection needle 112 into a target region.

After this needle-insertion operation, an injector motor 113 rotates forward, and this rotational force is decelerated by a deceleration gear box 114 directly connected to the injection motor 113, whereby a gear main shaft 115 of the deceleration gear box 114 is rotated. A front end of the gear main shaft 115 rotates a primary gear 116. This rotational force propagates to a tertiary gear 118 through a secondary gear 117. The tertiary gear 118 is coupled to a primary rod 119. Since the primary rod 119 is engaged with a secondary rod 120, rotational force of the primary rod 119 propagates to the secondary rod 120. Since the secondary rod 120 is engaged with a tertiary rod 121, a rotational force of the secondary rod 120 propagates to the tertiary rod 121. A rotational force of the tertiary rod 121 is restricted by a groove that is provided inside the cartridge holder 103, and the tertiary rod 121 moves in the direction of the arrow. When the tertiary rod 121 moves ahead in the syringe 101 by a predetermined amount, the secondary rod 120 that has rotated also pushes the syringe 101. Then, the tertiary rod 121 pushes a plunger in the syringe 101 so that a drug is pushed out of the injection needle 112, whereby an injection operation is performed. A dose is adjusted by counting rotations of the injection motor 113 by a rotation sensor 122.

The primary rod 119, the secondary rod 120, and the tertiary rod 121 have the same construction as the piston rod assembly described for the first embodiment.

After the injection operation, the injection motor 113 rotates backward to return the secondary rod 120 and the tertiary rod 121 to initial positions. Thereafter, the needle-insertion motor 105 rotates backward to move the slide cap 107 in a direction opposed to the arrow. The slide cap 107 is coupled to the inner frame assembly pat 110. When the needle-insertion motor 105 rotates backward, the inner frame assembly part 110 rotates in the direction opposed to the arrow. The inner frame assembly part 110 is coupled to the injection assembly part 111. Accordingly, the injection assembly part 111 moves in the direction opposed to the arrow together with the inner frame assembly part 110 when the needle-insertion motor 105 rotates backward, whereby the injection needle 112 is removed from the target region.

When the slide cap 107 returns to an initial position, the needle-removal sensor 108 is turned on to stop the needle-insertion motor 105, whereby a needle removal operation is completed.

Next, an external construction of the administration apparatus for medical use according to the present invention will be described with reference to FIG. 17.

In FIG. 17, reference numeral 123 denotes a power source switch for turning power on when using the administration apparatus, and turning power off after use.

Reference numeral 124 denotes an air releasing switch for starting air releasing in the syringe or injection needle.

Reference numeral 125 is a setting switch for setting such a dose of drug to be injected into a body.

Reference numeral 126 denotes a contact sensor for checking whether or not the administration apparatus contacts a region to be subjected to administration.

Reference numeral 127 denotes a display unit for displaying a set dose of drug to be injected into the body, and a condition in the administration apparatus, for example, an amount of remaining drug. Further, the display unit 127 notifies a user of abnormal operation or the like.

Reference numeral 128 denotes an injection needle port as an opening through which the injection needle passes during needle insertion and needle removal.

Next, an electrical circuit construction of the administration apparatus having the constructions shown in FIGS. 16 and 17 will be described with reference to FIG. 18. In FIG. 18, the same reference numerals as those shown in FIGS. 16 and 17 denote the same or corresponding parts.

Reference numeral 129 denotes a speaker for notifying a user of an end of operation, abnormal operation, or the like by voice.

Reference numeral 132 denotes an origin point sensor for detecting that the piston for injecting the drug in the syringe is positioned in an origin point.

Reference numeral 131 denotes a motor driver for outputting a signal for driving the injection motor 113 and the needle-insertion motor 105 according to a command from a microprocessor 130.

The microprocessor 130 is a controller which outputs a command for operating the injection motor 113 or the needle-insertion motor 105 by turning on the air releasing switch 124 or the administration switch 104 according to a program.

Next, a sequence of air releasing and drug injection by the microprocessor 130 of the administration apparatus according to the third embodiment will be described with reference to the flowchart shown in FIG. 19. When the air releasing switch 124 or the administration switch 104 is pressed, the sequence starts (step a1).

Next, it is judged whether or not the air releasing switch 124 is pressed (step a2). When the air releasing switch 124 is pressed, the process goes to step a3.

In step a3, the needle-insertion motor 105 is operated at a low speed using a reduction in driving voltage, or PWM (Pulse Width Modulation) control for changing an ON/OFF ratio of a pulse width of a signal, during a period from when the needle-removal sensor 108 is turned on to when the needle-insertion sensor 109 is turned on. Next, in step a4, the injection motor 113 is rotated forward by an amount required for air releasing, and air releasing is performed by moving the piston rods 119~121.

Next, in step a5, the needle-insertion motor 105 is rotated backward at a low speed to move the injection needle up to a position where the needle-insertion sensor 109 is on, thereby completing processing (step a9).

On the other hand, when not the air releasing switch 124 but the administration switch 104 is pushed in step a2, the process goes to step a6. In step a6, needle insertion is performed at a high speed to reduce pain of a patient associated with needle insertion.

Next, in step a7, the injection motor 113 is operated to inject a set dose of drug.

Next, in step a8, after this injection is ended, the needle-insertion motor 105 is rotated in a reverse direction at a high speed to move the injection needle from a position of a needle-insertion state to a position of a needle-removal state, thereby completing processing (step a9).

As described above, in the administration apparatus for medical use according to the third embodiment, when the air releasing switch 124 is pressed using the plural piston rods 119 to 121, air releasing can be easily performed by the motor with movements of the piston rods 119 to 121. Further, since the injection motor 113 is operated at a low speed during air releasing, it is possible to reduce a risk of a drug adhered to the injection needle or the like being splattered when the user visually checks air releasing.

Embodiment 4

Next, an administration apparatus for medical use according to a fourth embodiment of the present invention will be described. The administration apparatus according to the fourth embodiment always performs air releasing of a drug cartridge and/or an injection needle before performing drug administration to increase a level of safety of the apparatus. A construction of the apparatus according to the fourth embodiment is identical to that described with respect to FIGS. 16 to 18 and, therefore, repeated description is not necessary.

Figure 20:
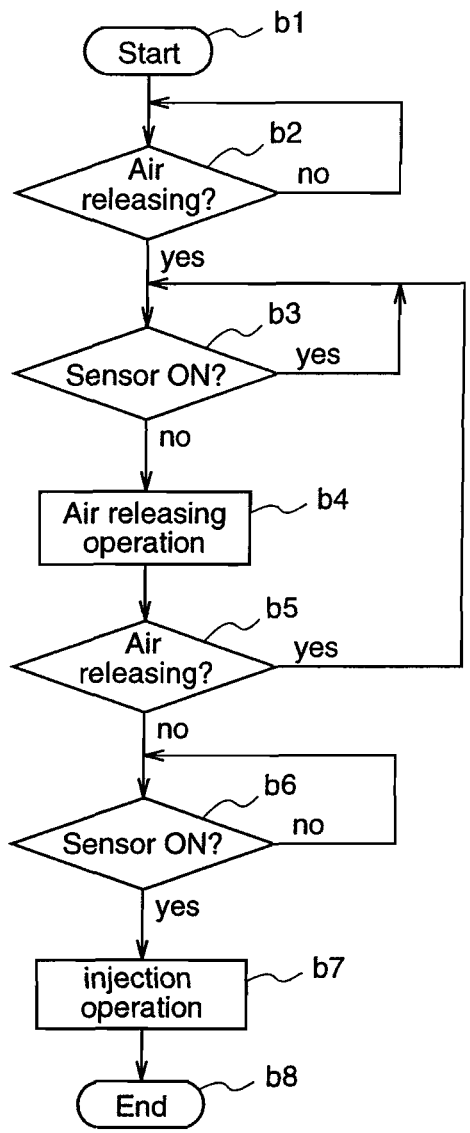
FIG. 20 is a flow chart for explaining an administration apparatus for medical use according to a fourth embodiment of the present invention.

Hereinafter, operation of the microprocessor 130 of the administration apparatus for medical use according to the fourth embodiment will be described with reference to FIG. 20.

When air releasing switch 124 or administration switch 104 is pressed, a sequence is started (step b1).

Initially, it is judged whether or not the air releasing switch 124 is pressed (step b2). When a pressed switch is not the air releasing switch 124 but the administration switch 104, step b2 is performed again. When the pressed switch is the administration switch 104, since administration is not performed, it is informed to a user that the administration switch 104 is pressed, using speaker 129 by voice or using display unit 127, or using both of the speaker 129 and the display device 127.

On the other hand, when the air releasing switch 124 is pressed in step b2, the process goes to step b3. In step b3, it is judged whether or not contact sensor 126 is on. Since there is a danger that the needle might be inserted into the user by mistake when the contact sensor 126 is on, step b3 is performed again. At this time, since air releasing is not performed when the contact sensor 126 is on, it is informed to the user that the contact sensor 126 is on, using the speaker 129 by voice or using the display device 127, or using both the speaker 129 and the display unit 127.

On the other hand, when the contact sensor 126 is not on in step b3, the process goes to step b4. In step b4, injection motor 113 is driven to release air in syringe 101 or injection needle 112.

Next, the user visually checks whether or not air releasing is satisfactorily performed, and presses the air releasing switch 124 again when it is not satisfactorily performed.

When air releasing is performed satisfactorily, the administration switch 104 is pressed. In step b5, it is judged which of the administration switch 104 and the releasing switch 124 is pressed. When the air releasing switch 124 is pressed, the process goes to step b3. When the administration switch 104 is pressed, the process goes to step b6.

In step b6, it is judged whether or not the contact sensor 126 is on. When the contact sensor 126 is not on, there is a possibility that the administration apparatus is not in contact with a predetermined target region of the user, and therefore, step b3 is performed again. Since no injection is performed when the contact sensor 126 is not on, it is informed to the user that the contact sensor 126 is not on, using the speaker 129 by voice or using the display device 127, or using both the speaker 129 and the display device 127. When the contact sensor 126 is on, the process goes to step b7.

In step b7, a set dose of drug is injected by driving the injection motor 113 to complete processing (step b8).

As described above, according to the fourth embodiment, the injection operation by pressing the administration switch 104 is enabled after detecting that the air releasing switch 124 is pressed before pressing the administration switch 104, using plural piston rods 119 to 121. Therefore, air releasing can be performed with reliability before drug injection to reduce a risk of injecting air into a human body, whereby a level of safety of the apparatus is increased.

Embodiment 5

An administration apparatus according to a fifth embodiment of the present invention will be described hereinafter. Since construction of the administration apparatus according to the fifth embodiment is identical to that described with respect to FIGS. 16 to 18, repeated description is not necessary.

Hereinafter, an electrical circuit structure of the administration apparatus according to the fifth embodiment will be described.

Figure 21:
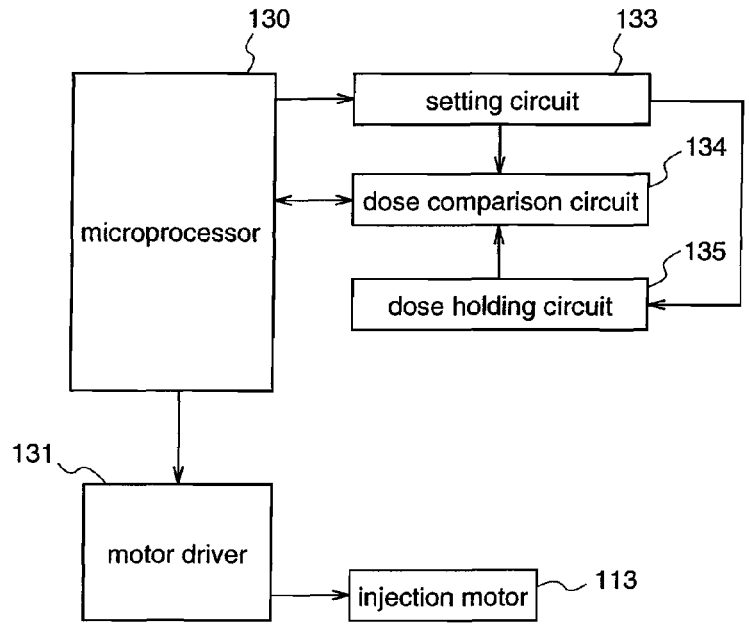
FIG. 21 is a block diagram for explaining connections of components in an administration apparatus for medical use according to a fifth embodiment of the present invention as an electric circuit.

FIG. 21 is a block diagram illustrating the construction shown in FIG. 18 to which a setting circuit 133, a dose comparison circuit 134, and a dose holding circuit 135, which are components peculiar to the fifth embodiment, are added, and the display unit 127 and the speaker 129 shown in FIG. 18 are omitted for simplification.

The setting circuit 133 is composed of an electronic circuit capable of storing an amount of operation of injection motor 113 which is obtained by converting an amount of injection outputted from microprocessor 130.

The dose storing circuit 135 is composed of an electronic circuit for storing doses of drug that have been administered in the past. To be specific, it stores a latest dose, or plural doses in the past, or an average of plural doses in the past.

The dose comparison circuit 134 is composed of an electronic circuit for comparing a dose that is set by the setting circuit 133 with a dose (doses) that is stored by the dose storing circuit 135.

Figure 22:
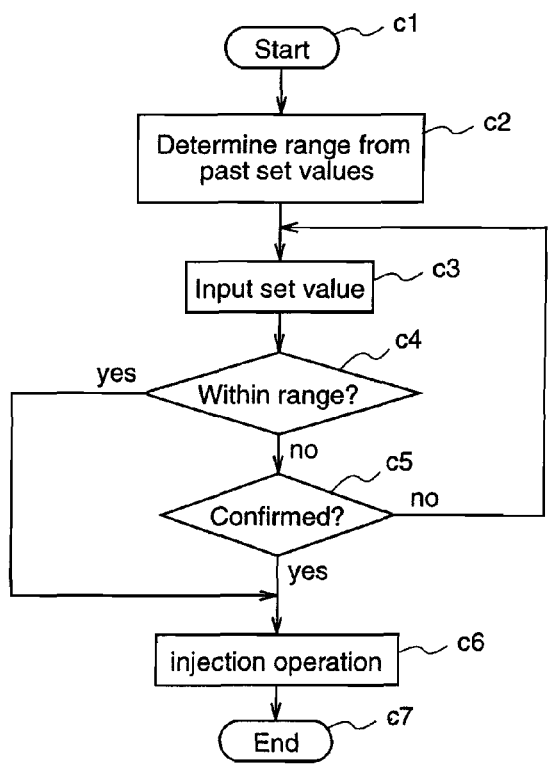
FIG. 22 is a flow chart for explaining operation of the administration apparatus according to the fifth embodiment.

Next, operation of the microprocessor 130 of the administration apparatus according to the fifth embodiment will be described with reference to FIG. 22.

When a user stands ready to set a dose, a sequence starts (step c1).

Initially, in step c2, a range of dose is calculated from the past set values that are stored in the dose holding circuit 135. The range of dose according to the past set values may be a range from −30% to +30% of the last dose, or a range that is obtained on basis of plural doses in the past. For example, using an average of data of past ten doses, a range from −30% to +30% of the average value is set as a range of dose. Moreover, a range of dose may be obtained by statistically calculating data of past ten doses using standard deviation or the like.

Next, in step c3, the user determines an amount of injection and sets the amount in the setting circuit 133.

Subsequently, in step c4, the dose comparison circuit 134 compares the value inputted by the user in step c3 with a value calculated in step c2. When a result of this comparison is within a predetermined range, the process goes to step c6. When the result of this comparison is out of the predetermined range; the process goes to step c5 to be described later.

In step c5, it is informed to the user that the set value is out of the predetermined range, using the speaker 129 by voice or using the display unit 127, or using both the speaker 129 and the display unit 127. Then, the user judges whether or not the process can be shifted to an injection step. When the user permits shifting to the injection step, the process goes to step c7. When the user refuses, the process goes back to step c3.

In step c6, injection of the set dose is performed by driving the injection motor 113 to complete the process (step c7).

In step c5, after informing the user that the set value is out of the predetermined range using the speaker 129 by voice or the display unit 127 or using both the speaker 129 and the display unit 127, the process may go to step c3 without confirmation by the user.

As described above, in the administration apparatus for medical use according to the fifth embodiment, when setting a dose using the setting switch 125, the set value is compared with past doses. When the result of this comparison is out of a predetermined range, it is informed to the user using the speaker 129 by voice or using the display unit 127, or using both the speaker 129 and the display unit 127. Depending on types of drugs, some drug might adversely affect a human body if a dose of the drug is significantly different from a proper dose. Therefore, when the dose changes significantly, a change of the dose is informed to the user before administration and then the user confirms the dose, or the user is inhibited to perform administration, whereby a level of safety of the motor-operated administration apparatus for medical use is increased.

Embodiment 6

Next, an administration apparatus for medical use according to a sixth embodiment of the present invention will be described. Since construction of the administration apparatus according to the sixth embodiment is identical to that described with respect to FIGS. 16 to 18, repeated description is not necessary.

Figure 23:
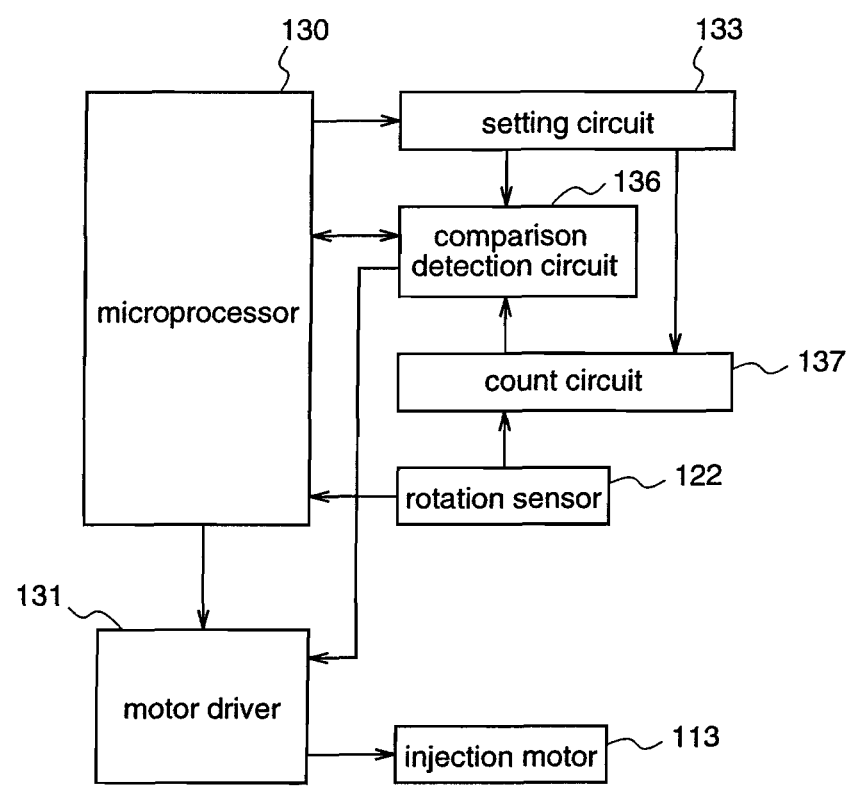
FIG. 23 is a block diagram for explaining connections of components in an administration apparatus for medical use according to a sixth embodiment as an electric circuit.
Figure 24:
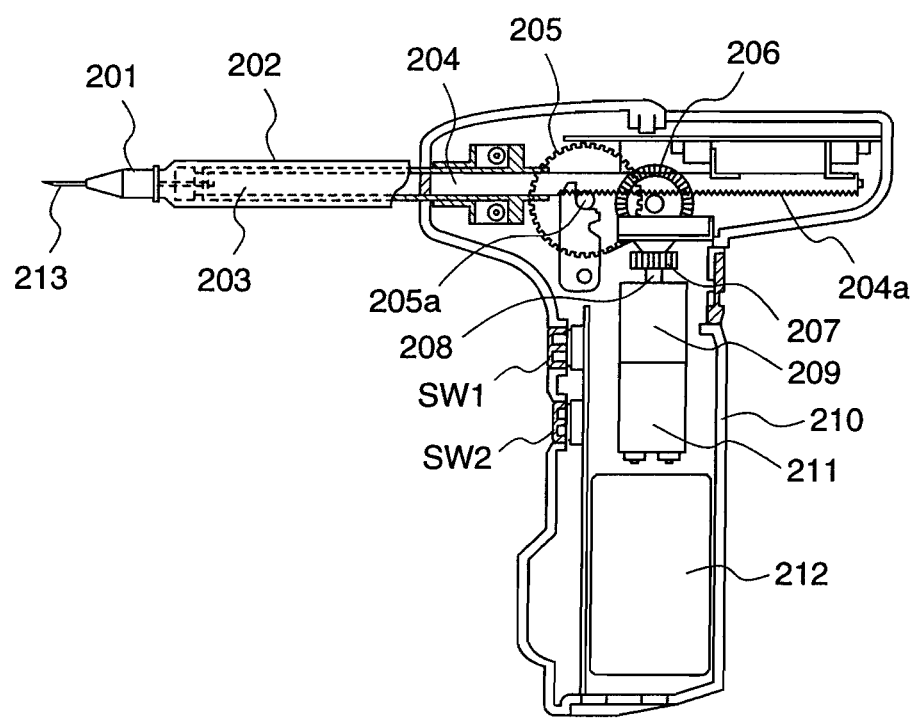
FIG. 24 is a diagram illustrating construction of a conventional administration apparatus for medical use.

An electrical circuit structure of the administration apparatus according to the sixth embodiment will be described with reference to a block diagram shown in FIG. 23. In FIG. 23, the construction shown in FIG. 18 further includes a setting circuit 133, a comparison detection circuit 136, and a count circuit 137 which are components peculiar to the sixth embodiment, and the display unit 127 and the speaker 129 shown in FIG. 18 are omitted for simplification.

Rotation sensor 122 is able to output operation of injection motor 113 as a frequency, and the frequency is output to microprocessor 130 and the count circuit 137.

The count circuit 137 is composed of an electronic circuit for counting signals from the rotation sensor 122, and it is able to count an amount of operation of the injection motor 113.

The setting circuit 133 is composed of an electronic circuit which is able to hold an amount of operation that is obtained by converting an amount of injection outputted from the microprocessor 130. Further, the setting circuit 133 is able to receive an instruction of an injection start or an injection end from the microprocessor 130, whereby it can make the count circuit 137 perform initialization.

A dose can be detected by measuring an amount of movement of the piston rod or measuring a time when the piston rod moves at a constant speed.

The comparison detection circuit 136 is composed of an electronic circuit for comparing a set value of the setting circuit 133 with a count value of the count circuit 137 to detect overdose or underdose of a drug. When the count value exceeds a predetermined value with respect to the set value before end of an operation, the comparison detection circuit 136 can stop operation of the motor driver 131, bypassing the microprocessor 130, and it can inform the microprocessor 130 that the predetermined value is exceeded. Further, when the count value is lower than a predetermined value with respect to the set value after the end of operation, the comparison detection circuit 136 can inform the microprocessor 130 that the count value is lower than the predetermined value.

In the above-mentioned construction, it is possible to directly observe an actual dose electronic-circuit-wise by the comparison detection circuit 136, in addition to observing a dose by program processing using the microprocessor 130. Therefore, even when a program of the microprocessor 130 is operated abnormally, the comparison detection circuit 136 detects an abnormal event to perform a process such as compulsory stopping of the motor driver 131, whereby overdose or underdose of drug can be avoided. As a result, double safeguards can be presented, whereby a level of safety of the motor-operated administration apparatus for medical use can be increased.

The administration apparatus for medical use according to the present invention is useful as a motor-operated injection apparatus or the like for a drug such as insulin, which provides easy replacement of drug cartridges and high portability.

What is claimed is:

1. An administration apparatus for medical use which performs administration of a drug, said apparatus comprising:
   a drug cartridge having an end closed with a plunger, and containing a drug inside;
   a cartridge holder for holding the drug cartridge;
   a piston rod for pressing the plunger in the drug cartridge to move the plunger;
   an injector motor which is connected to said piston rod, and drives said piston rod;
   a motor driver for controlling operation of said injector motor;
   a needle assembly for insertion of a needle into a target region and administering the drug emitted from the other end of the drug cartridge with movement of the piston rod;
   a dose setting circuit for setting, by a user, a dose of drug to be administered as a set value;
   a dose storing circuit storing a dose value range that is a range of dose amounts that is calculated from at least one dose amount that has been administered previously, and wherein the dose amount that has been administered previously is calculated on a basis of an amount of past movement of the piston rod driven by said injection motor;
   a dose comparison circuit for comparing a new set value with the dose value range stored in the dose storing circuit when the new set value is newly set by the dose setting circuit;
   a control circuit for performing control of the piston rod corresponding to a comparison result obtained by the dose comparison circuit, wherein the control circuit controls the motor driver to drive the piston rod when the new set value is within the dose value range, and wherein the control circuit suppresses the operation of the piston rod when the new set value is outside of the dose value range; and
   a notification unit for informing the user that the set value is outside of the new dose value range when the new set value is outside of the dose value range;
   wherein the dose value range is calculated based on a set percentage amount greater than and smaller than a certain dose value.

2. The administration apparatus of claim 1, wherein the certain dose value is an immediate past set value.

3. The administration apparatus of claim 1, wherein the certain dose value is an average value of past set values.

* * * * *